United States Patent
Lampman (12) 
(10) Patent No.: US 11,471,236 B1
(45) Date of Patent: Oct. 18, 2022

(54) PORTABLE ELECTRONEURODIAGNOSTIC CART

(71) Applicant: Robert Lampman, Fort Lauderdale, FL (US)

(72) Inventor: Robert Lampman, Fort Lauderdale, FL (US)

( * ) Notice: Subject to any disclaimer, the term of this patent is extended or adjusted under 35 U.S.C. 154(b) by 0 days.

(21) Appl. No.: 17/246,450

(22) Filed: Apr. 30, 2021

(51) Int. Cl.
*B65D 83/10* (2006.01)
*A61B 50/13* (2016.01)
*A61B 50/31* (2016.01)

(52) U.S. Cl.
CPC .............. *A61B 50/13* (2016.02); *A61B 50/31* (2016.02); *A61B 2560/0437* (2013.01)

(58) Field of Classification Search
CPC ... A61B 50/13; A61B 50/31; A61B 2050/311; A61B 2560/0437
USPC ........... 206/363, 570–572; 280/47.24, 47.29; 312/7.2, 249.13, 322, 327; 600/102
See application file for complete search history.

(56) References Cited

U.S. PATENT DOCUMENTS

| | | | |
|---|---|---|---|
| 2004/0032102 A1* | 2/2004 | Safari ................... | A61B 50/13 280/47.26 |
| 2004/0057821 A1* | 3/2004 | Samis ..................... | B62B 1/10 414/490 |
| 2004/0249673 A1* | 12/2004 | Smith ................. | A61B 5/02055 705/2 |
| 2005/0104308 A1* | 5/2005 | Barnes .................... | B62B 1/14 280/638 |
| 2012/0212116 A1* | 8/2012 | McRorie ................ | A61B 50/13 312/249.13 |
| 2019/0104922 A1* | 4/2019 | Kasumi ................... | A61B 1/05 |

* cited by examiner

*Primary Examiner* — Luan K Bui
(74) *Attorney, Agent, or Firm* — The Concept Law Group, PA; Scott M. Garrett; Scott D. Smiley (57) ABSTRACT

A wheeled intraoperative neuromonitoring transport device capable of portability and overhead airplane storage that comprises a lower frame that includes two outer legs and an inner support frame, an equipment holder secured about the lower frame, a back frame secured the lower frame, a frame coupled in sliding relation with the back frame between an opened and closed position, and an articulating computer tray carried by the frame via at least one pivoting joint.

20 Claims, 11 Drawing Sheets

PORTABLE ELECTRONEURODIAGNOSTIC CART

FIELD OF THE INVENTION

The present invention relates to a portable, collapsible medical carrier device, and more particularly to a portable, collapsible medical carrier device that is configured to store, transport and function as a work station for electroneurodiagnostic medical equipment and setup capable of utilizing pre-existing wire connections.

BACKGROUND OF THE INVENTION

A surgical procedure generally involves cutting into a patient. The surgical procedure may be a major procedure, such as entering a body cavity, removing organs, or altering normal anatomy. It can also be a minor procedure where the procedure occurs without extensive damage to tissue and small incisions.

In order to monitor patients in these surgical procedures, doctors incorporate intraoperative neurophysiologic monitoring ("IONM"). A trained clinician will utilize IONM equipment by monitoring electrical impulses to monitor in real-time the nervous system and specific pathways during surgery, providing surgeons with important information from the nervous system, particularly during brain, spinal cord, or peripheral nervous system surgeries.

For many surgeries, a technician is called in with their equipment to monitor a patient during the surgery. The technician will generally either carry their equipment in a travel bag or utilize a large cart that remains in the medical unit due to its size and weight.

Once in the operating room, the technician will setup all of the equipment on an operating room table. Due to the numerous wire connections required to use the IONM equipment for surgery, it is very cumbersome and time consuming to setup the IONM equipment before surgery and to put away the IONM equipment after surgery. The technicians are not presently able to utilize their equipment without first securing an OR table (which serves as a workstation) and making significant wire connections between the equipment before surgery, or utilizing equipment with non-portable carts.

Therefore, there is a need in the art for a device that allows the IONM operator to quickly and efficiently setup both before and after surgery. There is a need for a device that allows for the equipment to be stored, transported and utilized where the electrical connections are capable of being permanent. Additionally, there is a need for a device with the ability to travel, including on airplanes, safely and efficiently with the IONM equipment.

SUMMARY OF THE INVENTION

The present invention advantageously provides a portable, collapsible medical carrier device that is configured to store, transport and function as a work station for electroneurodiagnostic medical equipment and setup capable of utilizing pre-existing wire connections for the electroneurodiagnostic equipment.

According to an embodiment of the present invention, a principal object is to provide the electroneurodiagnostic carrier with a quick and efficient means for device set up and breakdown where electrical connections between the electrical devices is optionally permanent.

According to an embodiment of the present invention, another object is to afford a device that in the folded and collapsed state (the storage state) will fit in an overhead bin of an airplane.

Yet another object of the present invention is to provide a neuromonitoring cart to provide an integrated workstation for neuromonitoring during surgical procedures.

Yet another object of the present invention is to provide a medical equipment holder secured about the lower frame, the medical equipment holder configured to secure a base unit, two electrical stimulators, an amplifier, and a configuration to facilitate storage such that the medical equipment holder affords a race and/or track for looping wires that ultimately extend between the held device and an operating room table.

Yet another object of the present invention is to provide a wheeled intraoperative neuromonitoring transport device capable of easily being lifted and stowed in an overhead airplane compartment and/or in the trunk and/or body of a vehicle.

Yet further, another object of the present invention is to provide a wheeled intraoperative neuromonitoring transport device that includes a lower frame that includes two outer legs and an inner support frame, an equipment holder secured about the lower frame, a back frame secured perpendicular with the lower frame, a vertical frame coupled in vertical sliding relation with the back frame, the vertical frame slides between an opened and closed position, an articulating computer tray carried by the vertical frame via at least one pivoting joint, the articulating computer tray capable of opening after the vertical frame is slid open, and the inner support frame extends out in relation to the outer legs for support against toppling.

In yet another embodiment, the wheeled intraoperative neuromonitoring transport device the inner support frame that forms a rectangular frame includes two side frame members, a front frame member, and a rear frame member, each of the two side frame members secure on a forward portion with end portions of the front frame member and each of the two side frame members secure on a rear portion with end portions of the rear frame member. The wheeled intraoperative neuromonitoring transport device includes two wheels, each rotatable about an axis, mounted about rear corners of the lower frame, at least four feet mounted with the lower frame. The wheeled intraoperative neuromonitoring transport device includes a grippable handle positioned about the vertical frame. The wheeled intraoperative neuromonitoring transport device includes an equipment holder that includes a front panel and a rear panel forming an inner housing for medical equipment, and the front panel has multiple module receptacles. The module receptacles frictionally mount multiple neuromonitoring equipment. The wheeled intraoperative neuromonitoring transport device includes an articulating computer tray in a closed position secures a laptop from all sides behind the inner housing, and further includes a mouse tray that swivels out when the computer tray is in an opened position.

In yet a further embodiment of the present invention, the wheeled intraoperative neuromonitoring transport device includes at least one spring loaded plunger that maintains the vertical frame in a raised position.

In another embodiment of the present invention, the wheeled intraoperative neuromonitoring transport device includes a cover that encloses contents of the wheeled intraoperative neuromonitoring transport device. The cover may be a hard cover, a soft cover, or a combination thereof.

In another embodiment of the present invention, the wheeled intraoperative neuromonitoring transport device includes a telescoping travel handle secured about the back frame.

In one embodiment of the present invention, a wheeled intraoperative neuromonitoring transport device comprises a lower frame that includes two outer legs and an inner support frame, a medical equipment holder secured about the lower frame, the medical equipment holder configured to secure a base unit, an electrical stimulator, and an amplifier, a back frame secured perpendicular with the lower frame, a vertical frame coupled in vertical sliding relation with the back frame, an articulating computer tray carried by the vertical frame via at least one pivoting joint, two wheels, each rotatable about an axis, mounted about rear corners of the lower frame, and the inner support frame extends out in relation to the outer legs for support against toppling. The articulating computer tray pivots ninety degrees between open and closed.

In yet another embodiment of the present invention, the wheeled intraoperative neuromonitoring transport device includes a medical equipment holder that includes a plurality of module receptacles that frictionally mount a plurality of neuromonitoring equipment.

Other objects will become evident as the present invention is described in detail below.

BRIEF DESCRIPTION OF THE DRAWINGS

Embodiments of the present application are described herein in which similar elements are given similar reference characters, and a more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention advantageously provides a collapsible medical carrier device for transporting medical equipment such as intraoperative neuromonitoring systems.

Accordingly, the system and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Referring now to the drawings figures in which like reference designators refer to like elements.

Figure 1:
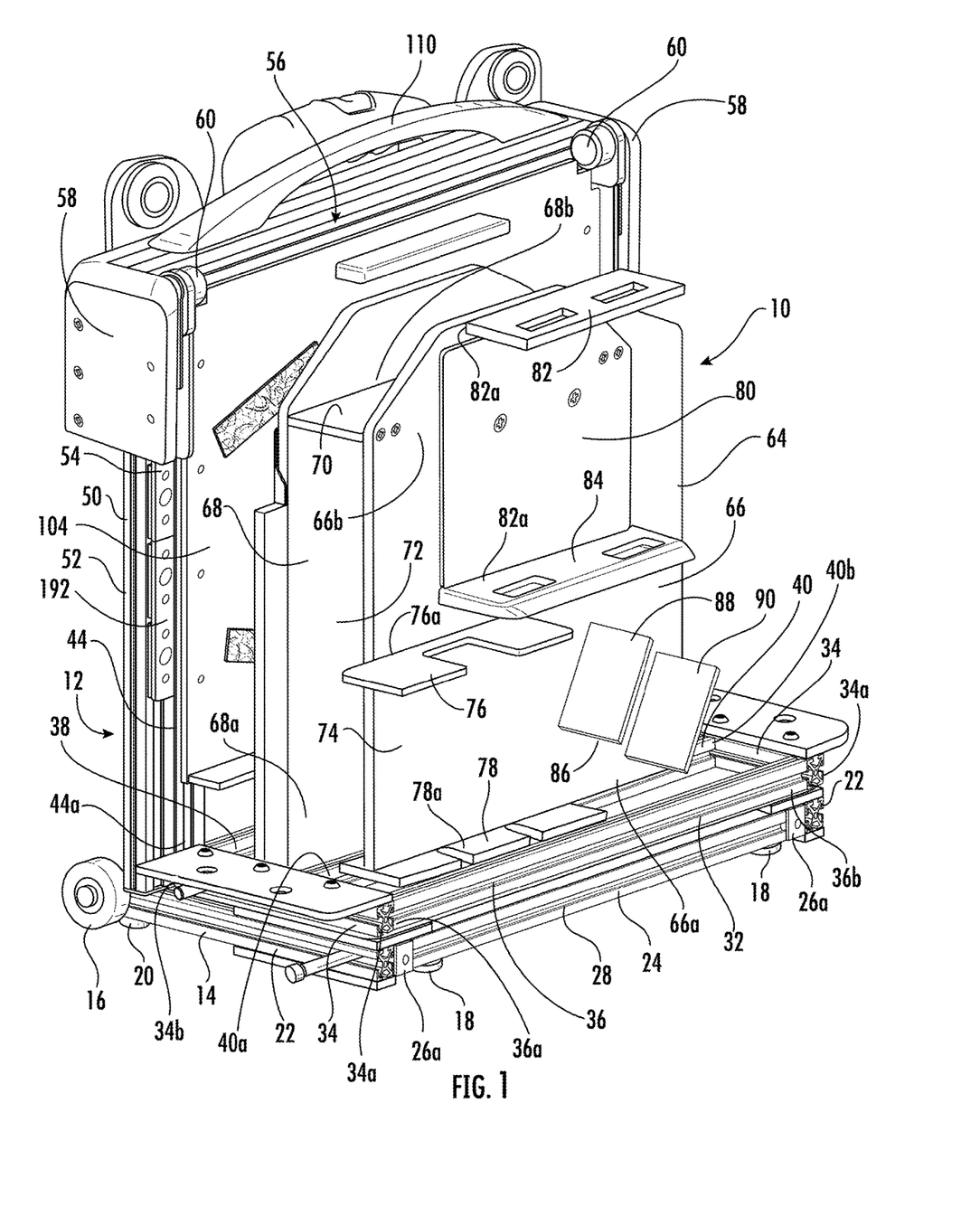
FIG. 1 is a front perspective view of a collapsible medical carrier device in accordance with the principles of the present embodiment in a collapsed position.
Figure 7:
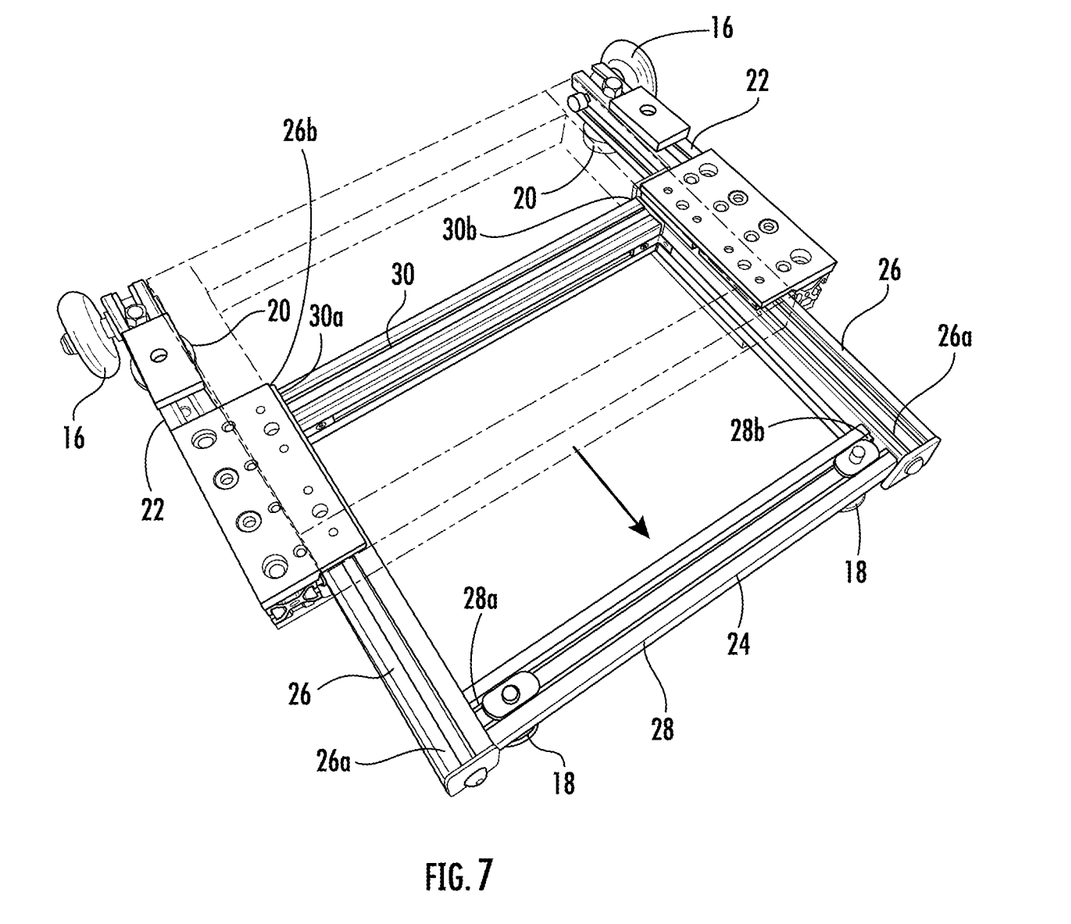
FIG. 7 of the collapsible medical carrier device in accordance with the principles of the present embodiment isolating a base portion.

FIGS. 1 and 7 shows an exemplary collapsible medical carrier device constructed in accordance with the principles of the present invention and designated generally as collapsible medical carrier device 10. The collapsible medical carrier device 10 transitions between a collapsed position for transport (see FIG. 1) and an open position for medical operation (see FIG. 3).

The collapsible medical carrier device includes a frame 12 with a lower frame base 14. Two wheels 16, each rotatable about an axis, are provided mounted near each rear left and right corner of the lower frame base 14 (see FIGS. 1 and 7).

The collapsible medical carrier device 10 rests upright on front feet 18 and back feet 20 (see FIGS. 1) located in each the corners of the lower frame base 14.

Figure 2:
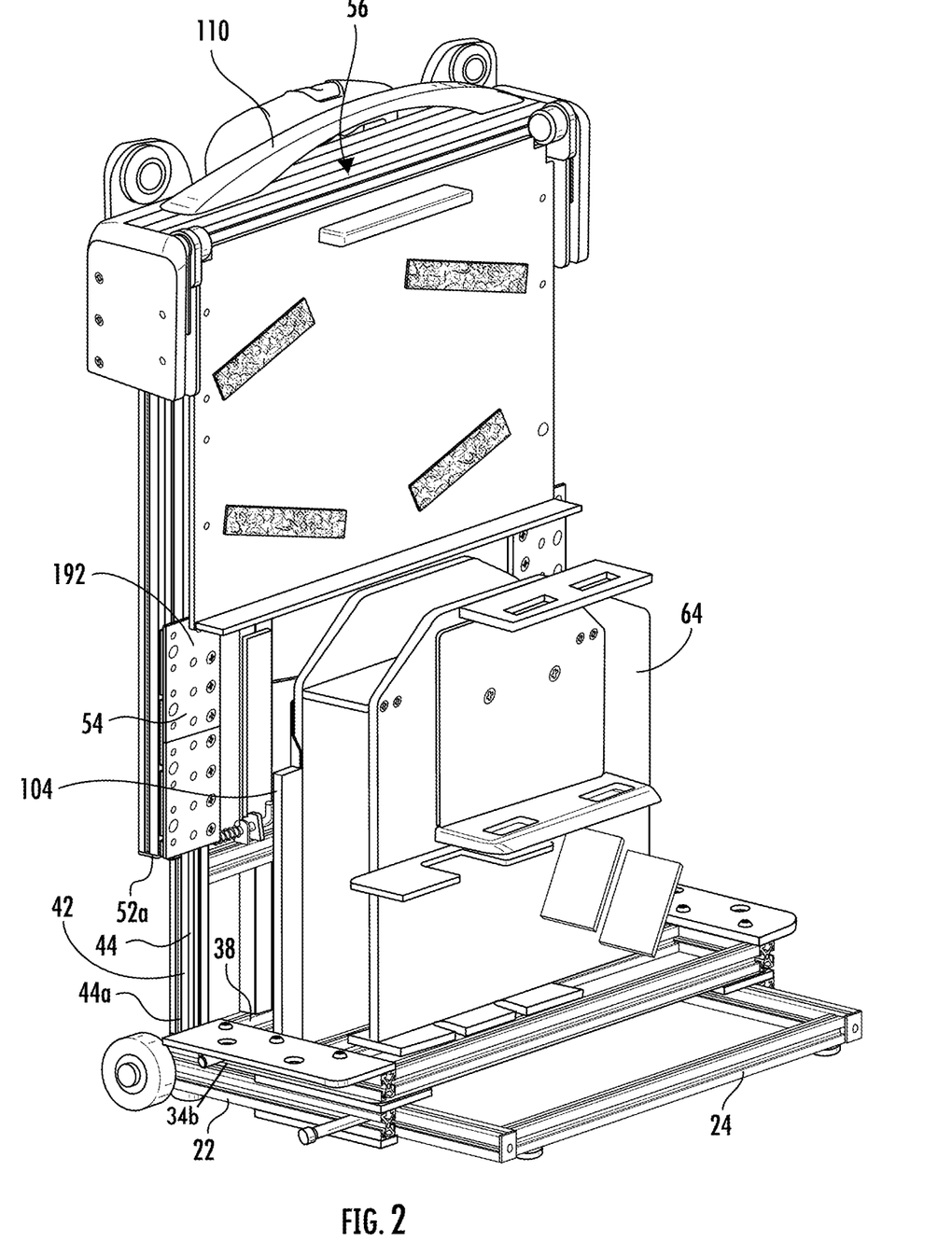
FIG. 2 is a front perspective view of the collapsible medical carrier device in accordance with the principles of the present embodiment in a partially opened position.

The lower frame base 14 includes outer legs 22 and an extendable inner support frame 24 (see FIGS. 1, 2, and 7). The inner support frame 24 slides laterally in relation to the outer legs 22. The inner support frame 24 moved to the open position (see FIG. 2) provides support against toppling by increasing the footprint of the lower frame base 14. The inner support frame 24 forming a rectangular frame includes two side frame members 26, a front frame member 28, and a rear frame member 30 (see FIGS. 1 and 7). Each of the two side frame members 26 secure on a forward portion 26a with end portions 28a, 28b of the front frame member 28 and each of the two side frame members 26 secure on a rear portion 26b with end portions 30a, 30b of the rear frame member 30.

An upper frame portion 32 of the lower frame base 14 is provided mounted over the outer legs 22 (see FIG. 1). The upper frame portion 32 includes two side frame members 34, a forward traverse frame member 36, a rear traverse frame member 38, and an inner traverse frame member 40. Each of the two side frame members 34 secure on a forward portion 34a with end portions 36a, 36b of the forward traverse frame member 36. The inner traverse frame member 40 secures on its ends 40a, 40b with the two side frame members 34. The two side frame members 34 (see FIGS. 1 and 8) are fastened along the outer legs 22.

A back vertical frame 42 (see FIGS. 1, 2, and 5) includes two vertical support posts 44. The lower end 44a of the first vertical support post 44 secure one end of the rear traverse frame member 38 and the lower end 44a of the second vertical support post 44 secure with the other end of the rear traverse frame member (i.e., on adjacent sides of the back vertical frame 42). The lower end 44a the two vertical support posts 44 secure with the rear portion 34b of the two side frame members 34. The back vertical frame 42 further includes an upper traverse vertical frame member 46 and an inner traverse vertical member 48. The upper traverse vertical member 46 secured on each end 46a, 46b with the upper ends two vertical support posts 44 (see FIGS. 3 and 5). The inner traverse vertical member 48 secures on each end 48a, 48b along a portion of each of the two vertical support posts 44.

Figure 3:
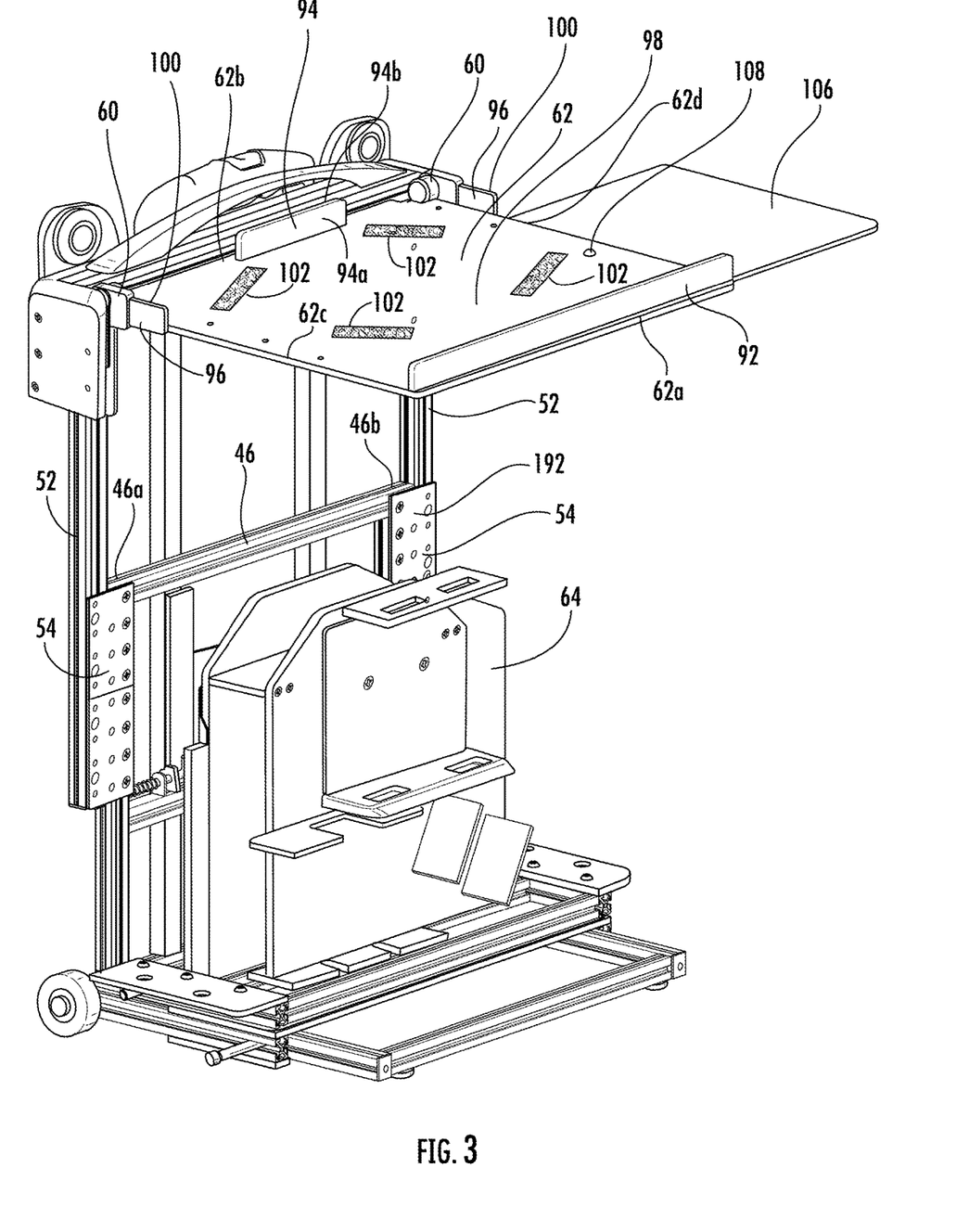
FIG. 3 is a front perspective view of the collapsible medical carrier device in accordance with the principles of the present embodiment in a fully opened position.

Referring now to FIGS. 1-3, a vertical carriage frame 50 is coupled in vertical sliding relation to the back vertical frame 42. The vertical carriage frame 50 includes two outer frame members 52. Each outer frame member 52 is secured in sliding relation with a vertical support post 44 coupled via linear bearings 54. The linear bearing 54 having an outer surface 192.

The vertical carriage frame 50 further includes an upper support frame 56 that secures between the upper ends of the two outer frame members 52. The upper support frame 56 carries a grippable handle 110 for allowing a user to lift and lower the vertical carriage frame 50 in relation to the back vertical frame 42.

Still referring to FIGS. 1-3, the two outer frame members 52 of the vertical carriage frame 56 carries outer joints 58 with two pivot arms 60 that carry a computer tray 62.

Yet still referring to FIGS. 1-3, the back vertical frame carries an equipment holder 64. The equipment holder 64 includes a front panel 66 and a rear panel 68. The rear panel 68 secures on its lower end 68a along at least a portion of the inner traverse frame member 40. The front panel 66 secures on its lower end 66a along at least a portion of the forward traverse frame member 36. An upper end 66a of the front panel 66 and an upper end 68b of the rear panel 68 are joined via an intermediate panel 70.

Figure 4:
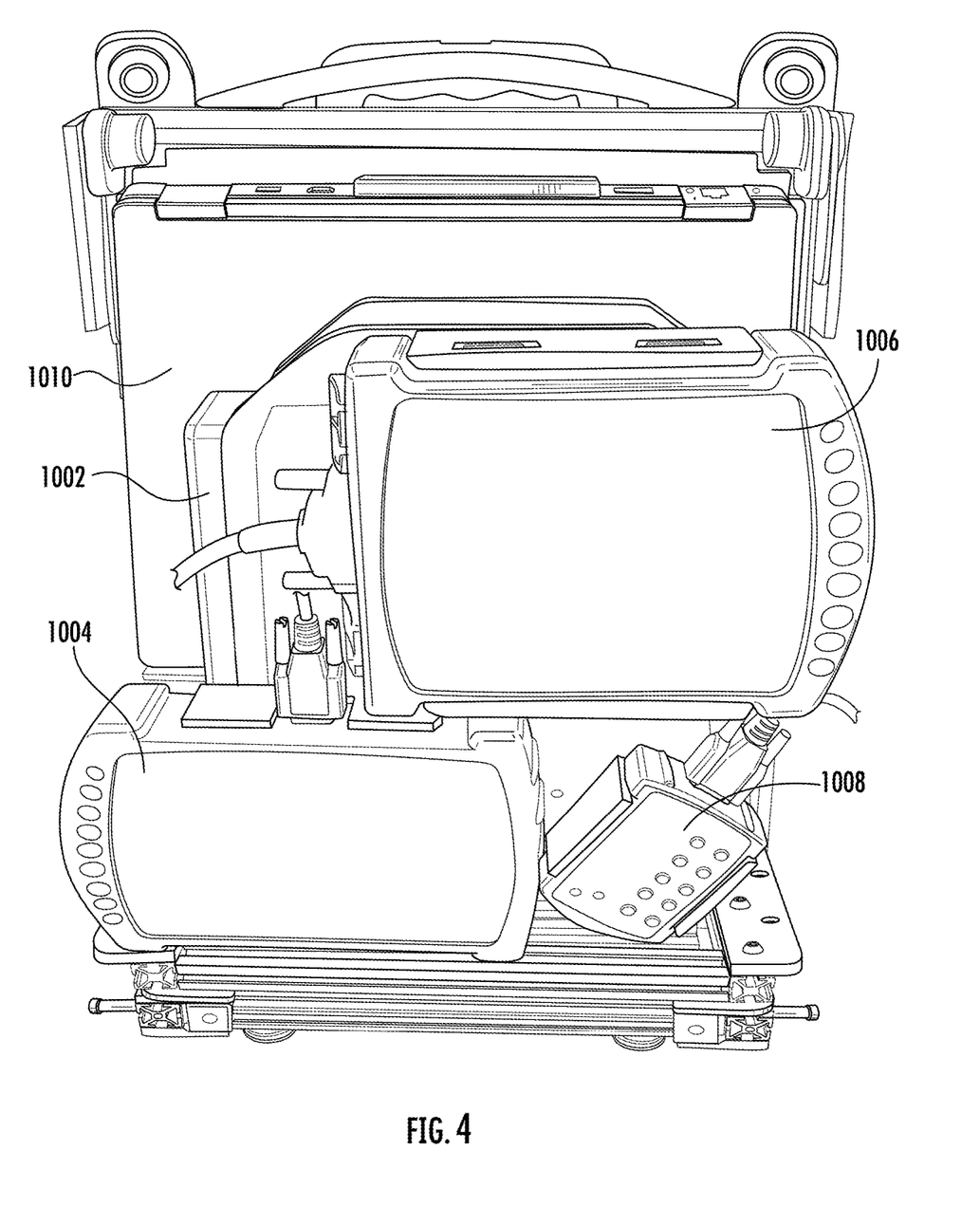
FIG. 4 is front view of the collapsible medical carrier device in accordance with the principles of the present embodiment in a collapsed position with IONM equipment secured therewith.

Referring now to FIGS. 1 and 4, the inner portion 72 of the equipment holder 64 provides a space for housing a medical module 1002. A vertical medical stimulator receptacle 74 is provided with an upper medical stimulator wall 76 and a lower medical stimulator wall 78 extend out from their proximal ends 76a, 78a respectively from the front panel 66 to frictionally engage a medical stimulator 1004. A vertical amplifier receptacle is provided with an upper amplifier wall 82 and a lower amplifier wall 84 that extend out from their proximal ends 82a, 84a respectively from the front panel 66 to frictionally engage a medical amplifier 1006. A vertical stimulator receptacle 86 is provided with first side stimulator wall 88 and a second side stimulator wall 90 that extend out from their proximal ends 88a, 90a respectively from the front panel 66 to frictionally engage a medical stimulator 1008.

In operation, the vertical receptacles 74, 80, 86 each secure respective medical equipment 1004, 1006, 1008 that may optionally be used while secured to their respective receptacle or any of the individual pieces of medical equipment 1004, 1006, 1008 can releasably detach from their receptacle such that the equipment can be moved closer to a operative patient.

Referring particularly to FIG. 3, a lower lip 92 is positioned at the front portion 62a of the computer tray 62, the lower lip 92 extending across the computer tray 62 and terminating at the left and right edge 62c and 62d has a lower edge 92a secured with the front portion 62a and terminates at an upper edge 92b for retaining a laptop on the computer tray 62. An upper lip 94 is positioned at the rear portion 62b of the computer tray 62 and has a lower edge 94a secured with the rear portion 62b and terminates at an upper edge 94b for retaining the laptop 1010 on the computer tray 62. The pivot arms 60 each include support posts 96 that support the computer tray 62. The pivot arms 60 extend outward along the left and right edge 62c and 62d from the upper surface 98 of the computer tray 62 providing side retaining lips 100 for retaining a laptop on the computer tray 62. The upper surface 98 includes retaining members 102 for securing the laptop 1010 to the upper surface 98.

In one non-limiting operation, the laptop tray 62 pivots ninety degrees(90°) between a closed position and an open position. To transition the laptop tray 62 from the open position to the closed position, the tray 62 is lifted upwards a few degrees past the ninety degrees and then the tray will drop downwards to the closed position.

In one non-limiting embodiment, the retaining members 102 are formed of hook and loop material with reciprocating hook and loop material on the bottom of the laptop computer 1010 (not shown) for securing the laptop 1010 to the upper surface 98 when in both an opened and closed position (see FIGS. 1, 3, and 4). The combination of the upper surface 98, lower lip 92, the upper lip 94, the support posts 96 with retaining lips 100, and rear panel 68 retain the laptop 1010 about the tray 62 when the collapsible medical carrier device 10 is closed (see FIG. 4), such as for transportation of the medical equipment to and from surgeries.

Referring particularly to FIG. 1, it can be seen that the vertical carriage frame 50 and the extendable inner support frame 24 are each shown in the closed position. In the closed position, the computer 1010 (not shown in FIG. 1) is impeded on each of its sides from falling from the tray 62 when the tray 62 is in the computer slot 104.

Referring particularly to FIG. 2, the collapsible medical carrier device 10 is provided shown transitioning between a fully open and/or fully closed position. It can be seen in FIG. 2 that the vertical carriage frame 50 is slid out upwards away from the computer slot 104 in an a partially open position with the computer tray 62 in the retracted position, and the extendable inner support frame 24 shown slid outward in relation to the outer legs 22 to the open position for support against toppling.

Referring particularly to FIG. 3, the collapsible medical carrier device 10 is provided fully opened with the laptop tray 62 locked open and with a mouse tray 106 extending out from underneath the tray 62. The mouse tray 106 secures at a point 108 with the laptop tray 62 in a swivel relation to allow the mouse tray 106 to be stowed away between the width of the outer legs 22.

Figure 5:
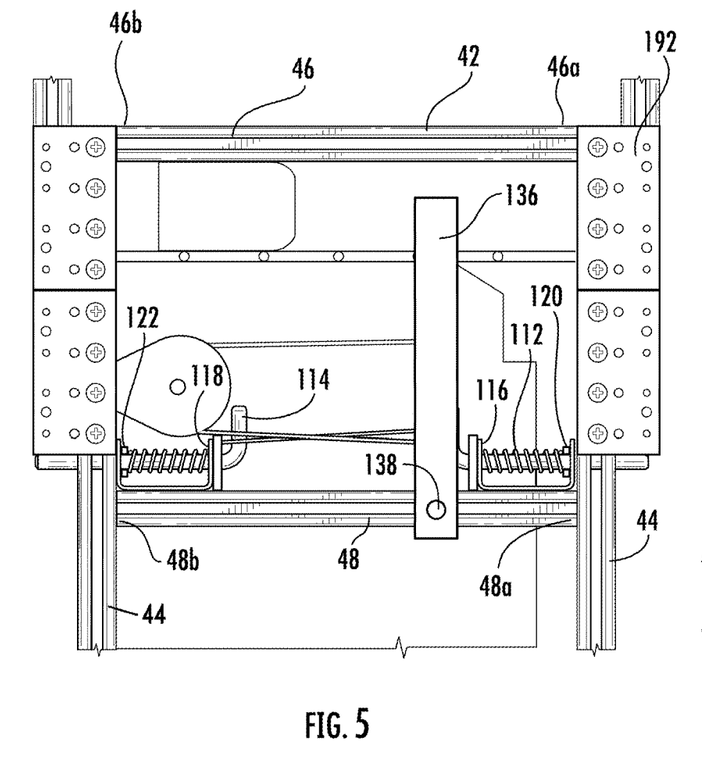
FIG. 5 is a partial rear view of the collapsible medical carrier device in accordance with the principles of the present embodiment in an opened position.

Referring now to FIGS. 2 and 5, a first plunger 112 and a second plunger 114 are retained via u-shaped plunger mount assemblies 116, 118. The first and second plunger 112, 114 each include a protrusion 120, 122 along the shaft of the plungers 112, 114. The protrusions 120, 122 prevent the plunger from passing through the distal ends 124, 126 of the u-shaped plunger mount assemblies 116, 118. Springs 128, 130 positioned along a portion of the plungers 112, 114 between the protrusions 120, 122 and the proximal ends 132, 134 of the mount assemblies 116, 118.

Figure 6:
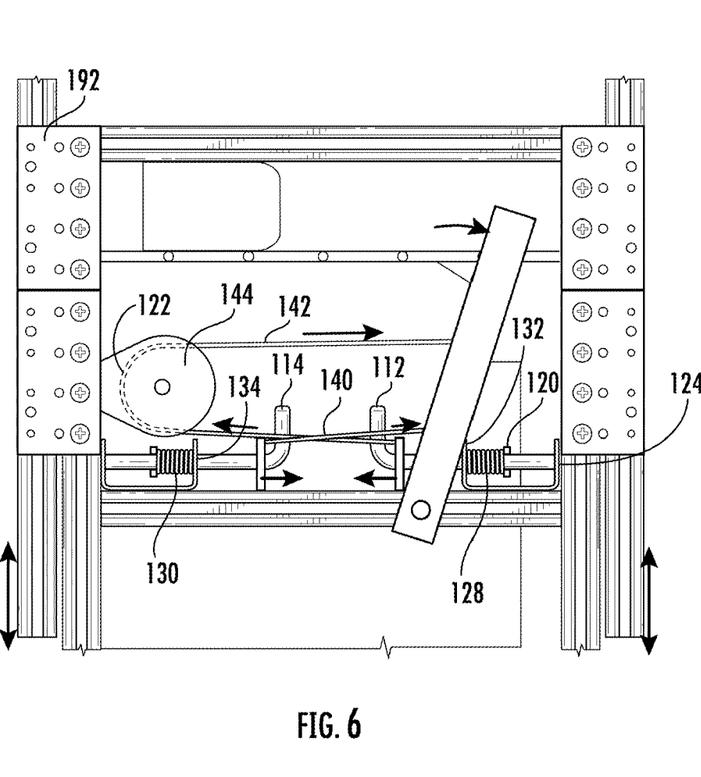
FIG. 6 is a partial rear view of the collapsible medical carrier device in accordance with the principles of the present embodiment transitioning from an open to a collapsed position.

Referring now to FIGS. 5 and 6, in operation, the springs 128, 130 provide a lateral force against the protrusions 120, 122 to urge the plungers outward until that settle under the lower ends 52a of the outer frame members 52 when the vertical frame carriage 50 is lifted by a user to the fully opened position (shown in FIG. 2).

Still referring to FIGS. 5 and 6, a lever arm 136 is provided rotatably mounted at a point 138 with the inner traverse vertical member 48. A first cord 140 is secured interposed with the second plunger 114 and the lever arm 136 such that rotating the lever arm 136 causes the plunger 114 to retract inwards (see FIG. 6). A second cord 142 is secured interposed between the plunger 112 and the lever arm 136 with an intermediary pully 144, the intermediary pully 144 mounted with one of the vertical support posts 44, such that rotating the lever arm 136 causes the plunger 112 to retract inwards (see FIG. 6).

In operation, when the lever arm 136 is rotated from the standing position shown in FIG. 5 to the rotated position shown in FIG. 6, the plungers 112, 114 are retracted to allow the vertical carriage frame 50 to drop downwards from the partially open position shown in FIG. 2 to the closed position shown in FIG. 1.

Figure 8:
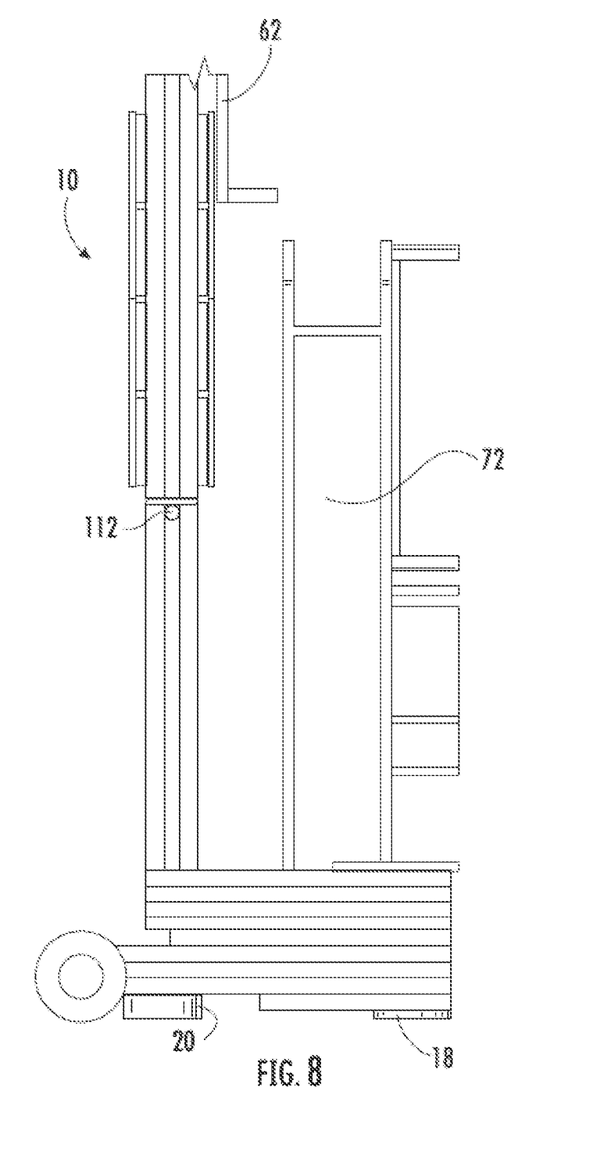
FIG. 8 is a side isolated view of the collapsible medical carrier device in accordance with the principles of the present embodiment in a partially opened position.

Referring now to FIG. 8, a partial side view of the collapsible medical carrier device 10 is shown in a partially opened position with the tray 62 in the closed position. The plunger 112 is shown extended maintaining the vertical carriage frame 50 in the open position. One of the front feet 18 and one of the back feet 20 is shown supporting the collapsible medical carrier device 10 in the upright position. In operation, the wheels 16 engage the ground and disengage the feet 18, 20 when a user tilts the collapsible medical carrier device 10 from the upright position.

Referring now to FIGS. 9-12, in a non-limiting embodiment, a case 146 is provided for enclosing the equipment during transportation and/or storage. The present embodiment is a hard shell 148 covered with fabric. A first handle 150 is provided about an upper surface 152 of the case 146. A second handle 154 is provided about a side surface 156 of the case 146. While the case is depicted with two handles 150, 154 on the case 146, it is within the spirit and scope of the present invention to provide additional like handles on the outer surfaces of the case 146 at various positions to allow a user to grip and/or turn the bag with two hands and/or at different angles and orientations.

Still referring to FIGS. 9-12, case guide pins 146 are secured to a portion of each of the outer legs 22 for receiving and guiding the case onto the frame 12. In operation, the case guide pins 146 allow the lower edges 158, 160 of the case 146 to rest on the case guide pins 146 as the user slides the case towards the back vertical frame 42.

Figure 9:
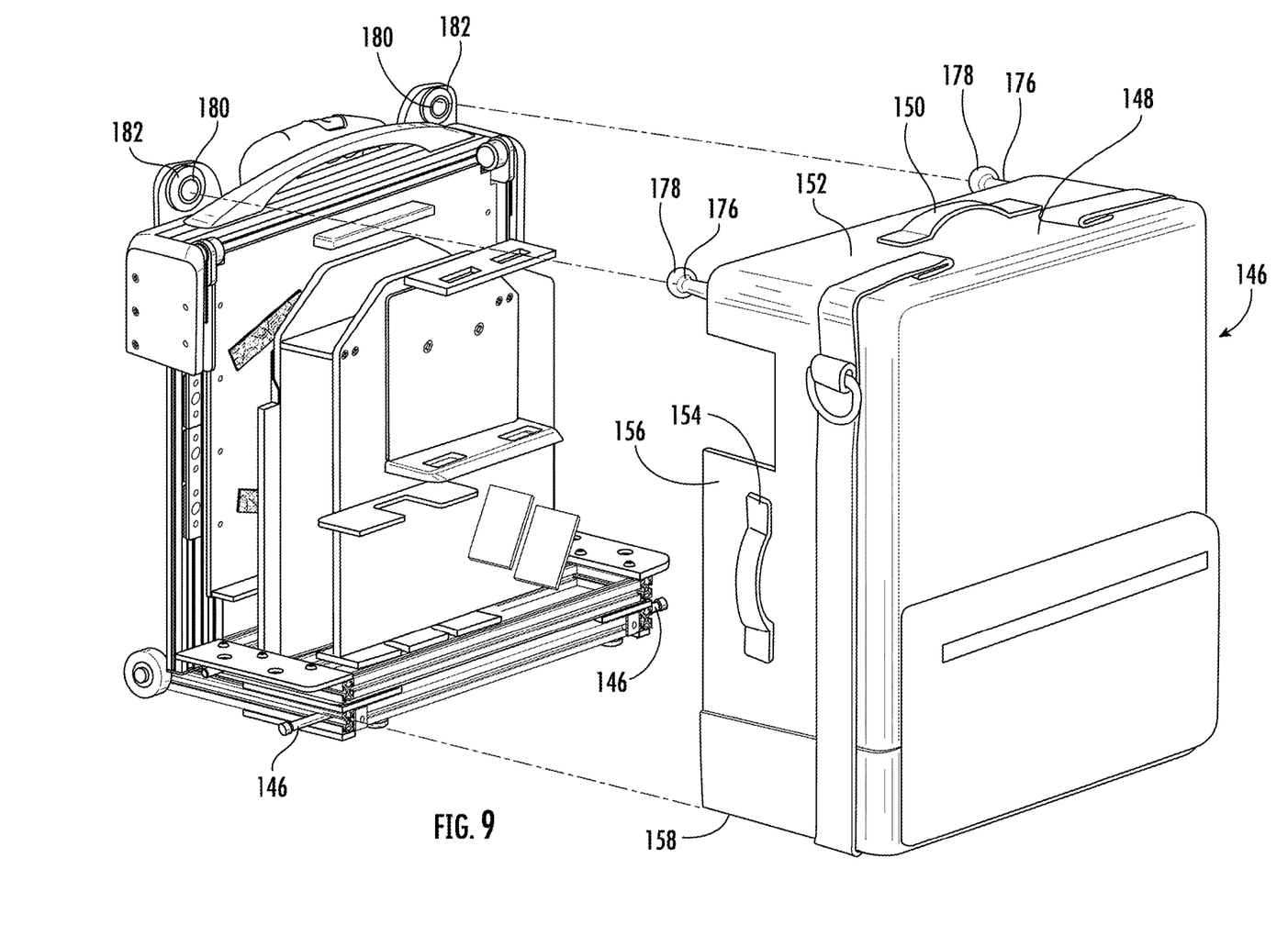
FIG. 9 is a front perspective view of the collapsible medical carrier device in accordance with the principles of the present embodiment in a collapsed position with the introduction of an encasement.
Figure 10:
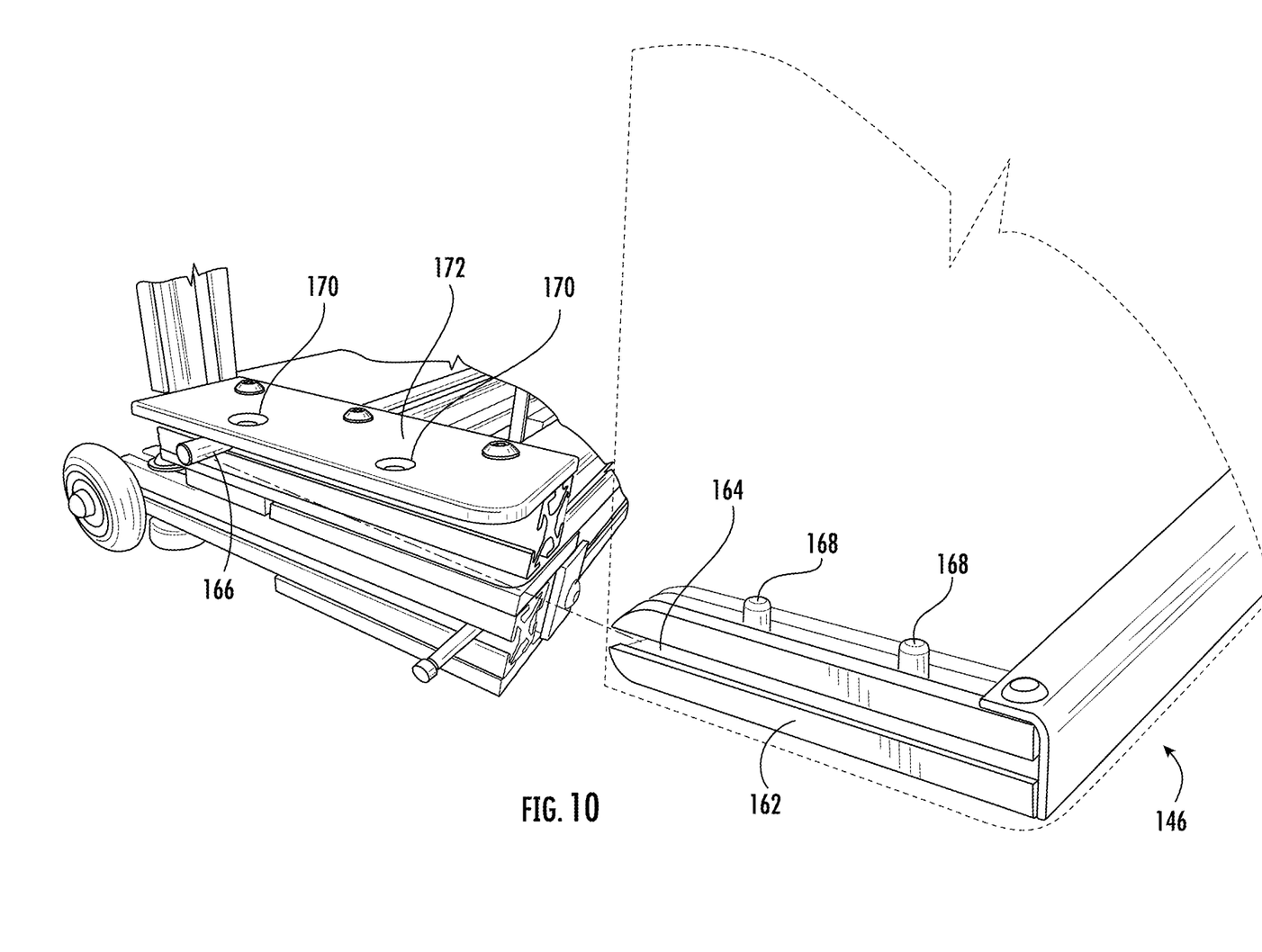
FIG. 10 is a side isolated perspective view of the collapsible medical carrier device in accordance with the principles of the present embodiment with the introduction of an encasement.
Figure 11:
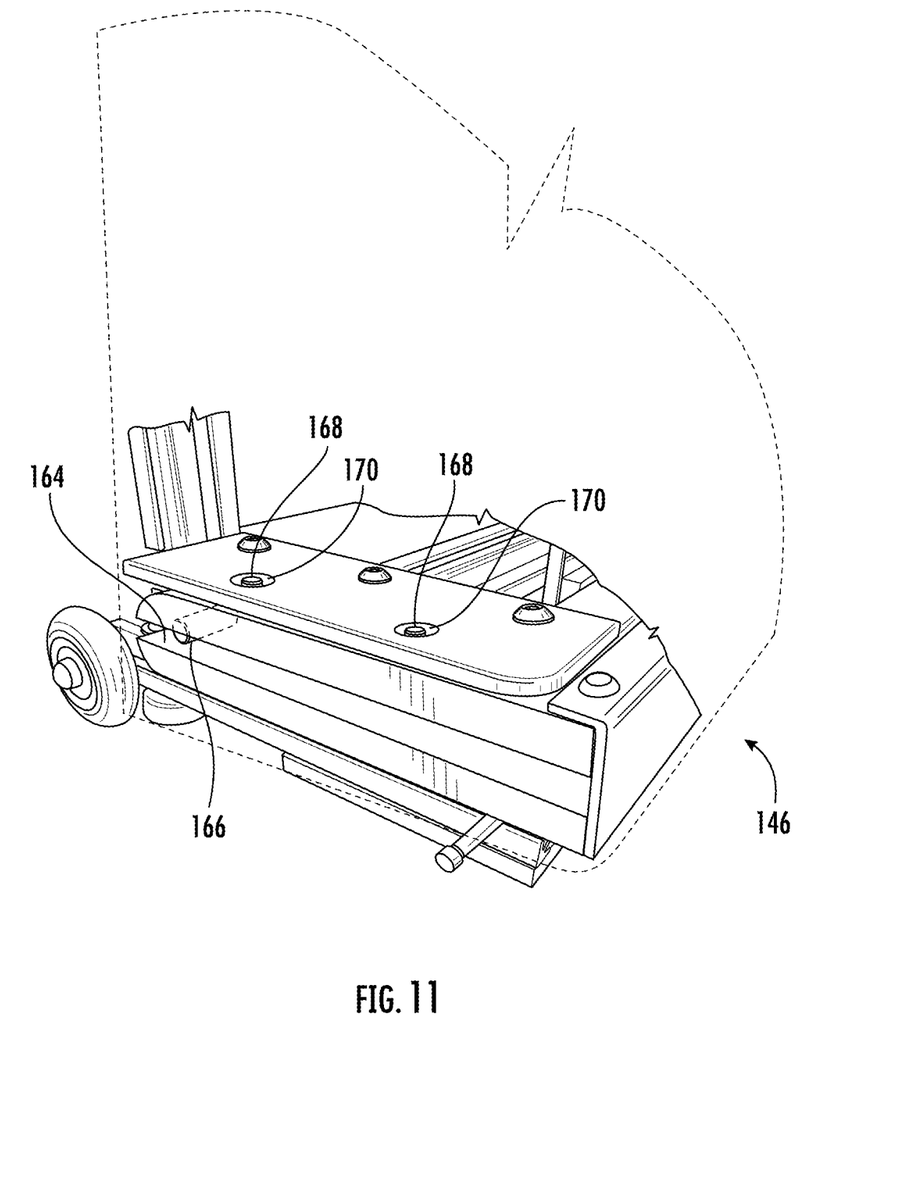
FIG. 11 is a side isolated perspective view of the collapsible medical carrier device in accordance with the principles of the present embodiment with a portion of an encasement shown with phantom lines.

Referring to FIGS. 10-11, the side surface 156 of the hard shell 148 is provided in phantom lines such that the lower left inner mechanism 162 is illustrated (A lower right inner mechanism is not shown but is a provided as a mirror image on the opposite side 174 of the case 146). As the lower edges 158, 160 slide along the case guide pins 146 towards a closed position, a forward cavity 164 on each of the left and right side of the case 146 receives a locking pin 166. Once the forward cavity 164 on each of the left and right side of the case 146 receives the locking pin 166, the case 146 is rotated upwards such that the locking teeth 168 engage the locking apertures 170 provided on the locking plate 172. One locking plate 172 is provided on each of the two side frame members 34 for receiving the locking teeth 168 positioned on each of the left and right side 156, 174 (see FIGS. 9 and 12) of the case 146.

Figure 12:
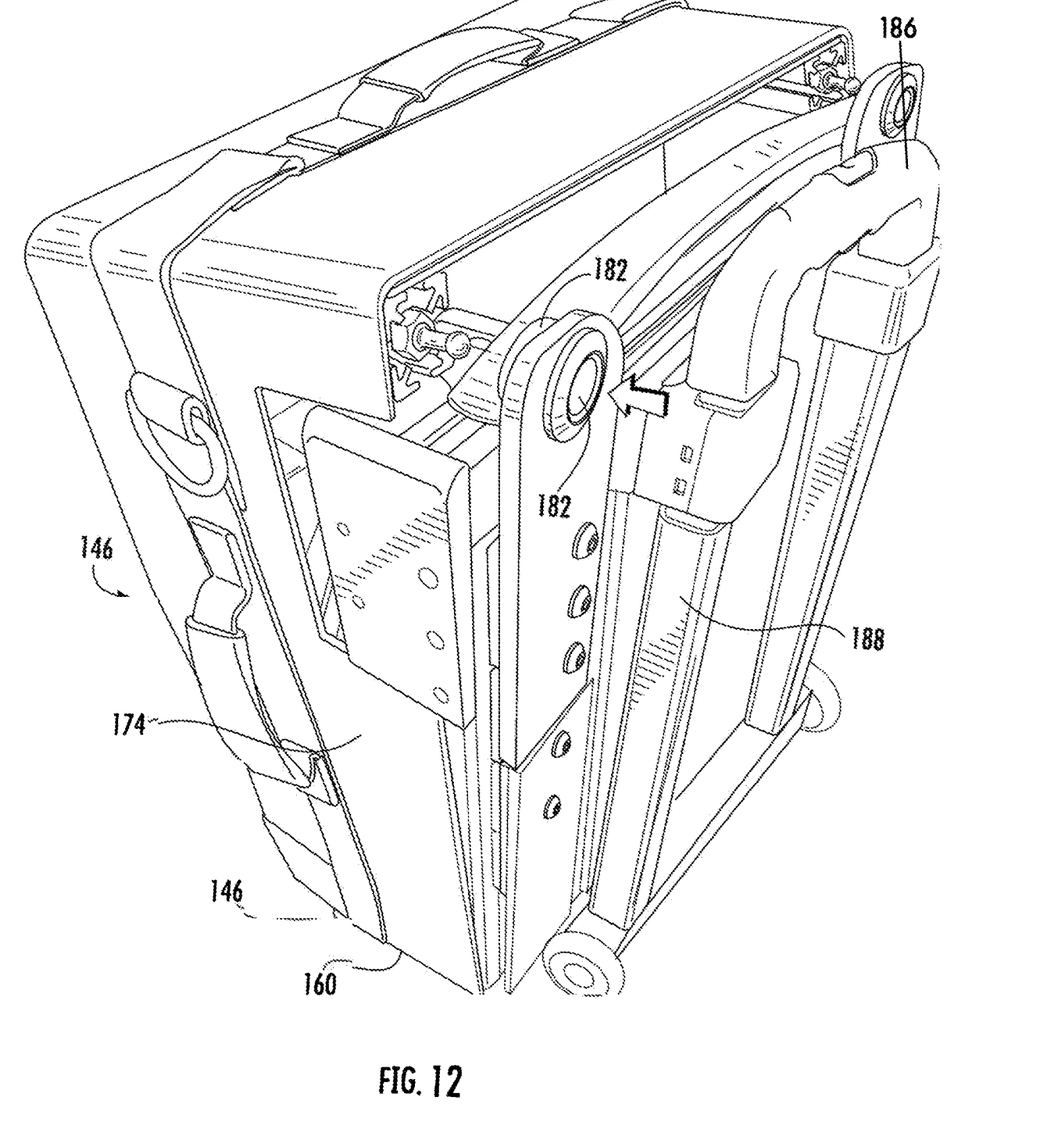
FIG. 12 is a side perspective view of the collapsible medical carrier device in accordance with the principles of the present embodiment with the encasement being released and/or engaged.

Referring now to FIGS. 9 and 12, the upper portion of the case 146 includes fastening pins 176. The fastening pins 176 are each formed having a ball portion 178 that are received into the sockets 180 of the socket body 182. The sockets are secured with the vertical carriage frame 50. As the case 146 is rotated upwards such that the locking teeth 168 engage the locking apertures 170, the ball portions 178 lock into the sockets 180. The sockets 180 include a push button release 184 opposite the socket 180, operating such that when the push button release 184 is depressed towards the socket 180, the ball portion is released from the socket 180 (see FIG. 12).

Referring now to FIG. 12, the back vertical frame 42 (FIG. 2) carries a telescoping handle 186 that when ascended from the closed position allows a user to roll the bag for transportation. When the telescoping handle 186 is retracted, the tube sections store within the handle case 188.

While the instant invention depicts 80/20 metal frame members held together with various t-nuts, bolts, and other connectors, as well as facilitating motion with linear bearings and locking hinges, alternate framing and motion members are contemplated and are within the spirit and scope of the instant invention.

In a non-limiting embodiment, the outer legs 22 and an extendable inner support frame 24 are secured together via linear bearing members 190 (see FIGS. 1, 2, and 7). The inner support frame 24 slides laterally in relation to the outer legs 22 via the linear bearings 190.

In a non-limiting embodiment, the vertical carriage frame 50 is coupled in vertical sliding relation to the back vertical frame 42 via linear bearing members 54.

As used herein, when the term "and/or" is used, it shall include all combinations of one or more of the associated described items.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are contemplated in light of the above teachings without departing from the scope and spirit of the invention. It will be readily apparent that various changes may be made thereto without departing from the spirit and scope of the disclosure or sacrificing all of its material advantages. The examples and embodiments described herein are merely exemplary of the instant disclosure.

What is claimed is:

1. A wheeled intraoperative neuromonitoring transport device comprising:
   a lower frame that includes two outer legs and an inner support frame;
   an equipment holder secured about said lower frame;
   a back frame secured perpendicular with said lower frame;
   a vertical frame coupled in vertical sliding relation with said back frame, said vertical frame slides between an opened and closed position;
   an articulating computer tray carried by said vertical frame via at least one pivoting joint, said articulating computer tray capable of opening after said vertical frame is slid open; and
   wherein said inner support frame extends out in relation to said outer legs for support against toppling.

2. The wheeled intraoperative neuromonitoring transport device of claim 1 wherein said inner support frame forming a rectangular frame includes two side frame members, a front frame member, and a rear frame member, each of said two side frame members secure on a forward portion with end portions of said front frame member and each of said two side frame members secure on a rear portion with end portions of said rear frame member.

3. The wheeled intraoperative neuromonitoring transport device of claim 2 further comprising two wheels, each rotatable about an axis, mounted about rear corners of said lower frame.

4. The wheeled intraoperative neuromonitoring transport device of claim 3 further comprising at least four feet mounted with said lower frame.

5. The wheeled intraoperative neuromonitoring transport device of claim 1 further comprising a grippable handle positioned about said vertical frame.

6. The wheeled intraoperative neuromonitoring transport device of claim 1 wherein said equipment holder comprising a front panel and a rear panel forming an inner housing for medical equipment, and wherein said front panel having a plurality of module receptacles.

7. The wheeled intraoperative neuromonitoring transport device of claim 6 wherein said plurality of module receptacles frictionally mount a plurality of neuromonitoring equipment.

8. The wheeled intraoperative neuromonitoring transport device of claim 7 wherein said articulating computer tray in a closed position secures a laptop from all sides behind said inner housing.

9. The wheeled intraoperative neuromonitoring transport device of claim 8 further comprising hook and loop material positioned on a surface of said articulating computer tray for securing a laptop thereon.

10. The wheeled intraoperative neuromonitoring transport device of claim 9 further comprising a mouse tray that swivels out when said articulating computer tray is in an opened position.

11. The wheeled intraoperative neuromonitoring transport device of claim 1 further comprising at least one spring loaded plunger that maintains said vertical frame in a raised position.

12. The wheeled intraoperative neuromonitoring transport device of claim 1 further comprising a cover that encloses contents of said wheeled intraoperative neuromonitoring transport device.

13. The wheeled intraoperative neuromonitoring transport device of claim 1 further comprising a telescoping travel handle secured about said back frame.

14. A wheeled intraoperative neuromonitoring transport device comprising:
- a lower frame that includes two outer legs and an inner support frame;
- a medical equipment holder secured about said lower frame, said medical equipment holder configured to secure a base unit, an electrical stimulator, and an amplifier;
- a back frame secured perpendicular with the lower frame;
- a vertical frame coupled in vertical sliding relation with said back frame;
- an articulating computer tray carried by the vertical frame via at least one pivoting joint;
- two wheels, each rotatable about an axis, mounted about rear corners of the lower frame; and
- wherein the inner support frame extends out in relation to the outer legs for support against toppling.

15. The wheeled intraoperative neuromonitoring transport device of claim 14 wherein said articulating computer tray pivots ninety degrees between open and closed.

16. The wheeled intraoperative neuromonitoring transport device of claim 15 wherein said articulating computer tray pivots ninety degrees between open and closed.

17. The wheeled intraoperative neuromonitoring transport device of claim 14 wherein said medical equipment holder includes a plurality of module receptacles that frictionally mount a plurality of neuromonitoring equipment.

18. The wheeled intraoperative neuromonitoring transport device of claim 17 wherein said articulating computer tray in a closed position with said medical equipment holder secures a laptop from all sides.

19. A wheeled intraoperative neuromonitoring transport device comprising:
- a lower frame that includes two outer legs and an inner support frame;
- a medical equipment holder secured about said lower frame, said medical equipment holder configured to secure a base unit, two electrical stimulators, an amplifier;
- a back frame secured perpendicular with the lower frame;
- a vertical frame coupled in vertical sliding relation with said back frame;
- an articulating computer tray carried by the vertical frame via at least one pivoting joint;
- two wheels, each rotatable about an axis, mounted about rear corners of the lower frame; and
- wherein the inner support frame extends out in relation to the outer legs for support against toppling.

20. The wheeled intraoperative neuromonitoring transport device of claim 19, wherein said wheeled intraoperative neuromonitoring transport device capable of stowing in an overhead airplane compartment.

* * * * *